US012797069B2

(12) United States Patent
Mei

(10) Patent No.: US 12,797,069 B2
(45) Date of Patent: Nov. 17, 2026

(54) DISTAL MEDIAL TIBIAL HEMI-EPIPHYSIODESIS BLOCKING STAPLE AND SUPPORTING TOOLS

(71) Applicant: Haibo Mei, Changsha City (CN)

(72) Inventor: Haibo Mei, Changsha City (CN)

( * ) Notice: Subject to any disclaimer, the term of this patent is extended or adjusted under 35 U.S.C. 154(b) by 166 days.

(21) Appl. No.: 18/798,908

(22) Filed: Aug. 9, 2024

(65) Prior Publication Data

US 2026/0041424 A1 Feb. 12, 2026

(51) Int. Cl.
*A61B 17/072* (2006.01)

(52) U.S. Cl.
CPC .............................. *A61B 17/07207* (2013.01)

(58) Field of Classification Search
CPC ..... A61B 17/06; A61B 17/064; A61B 17/068; A61B 17/0642
See application file for complete search history.

(56) References Cited

U.S. PATENT DOCUMENTS

| | | | | |
|---|---|---|---|---|
| 11,020,110 B1 * | 6/2021 | Blair | A61B 17/0642 | |
| 2004/0138705 A1 * | 7/2004 | Heino | A61B 17/064 | 606/219 |
| 2019/0000451 A1 * | 1/2019 | Majors | A61B 17/10 | |

* cited by examiner

*Primary Examiner* — Christopher J Beccia
(74) *Attorney, Agent, or Firm* — Thomas | Horstemeyer, LLP

(57) ABSTRACT

Provided are a distal medial tibial hemi-epiphysiodesis blocking staple and supporting tools. The distal medial tibial hemi-epiphysiodesis blocking staple includes a tibia arm, an epiphyseal arm and a connecting section. The connecting section is connected with the tibial arm and the epiphyseal arm to form a similar U-shape. The tibial arm and the epiphyseal arm are arranged in parallel and in arc transition with the connecting section to limit a spacing between the distal tibia and the epiphysis. Inverted tooth portions for preventing the hemi-epiphysiodesis distal medial tibial staple from withdrawing are uniformly distributed on the tibial arm and the epiphyseal arm.

20 Claims, 4 Drawing Sheets

DISTAL MEDIAL TIBIAL HEMI-EPIPHYSIODESIS BLOCKING STAPLE AND SUPPORTING TOOLS

TECHNICAL FIELD

The present disclosure relates to the technical field of epiphysiodesis blocking, and in particular to a distal medial tibial hemi-epiphysiodesis blocking staple and supporting tools.

BACKGROUND

Structures and growth of skeletons in children and adults are different. The growth of limb long bone of the children mainly depends on the growth of epiphyseal plates located at both ends of the long bone, and the growth potential of the epiphyseal plates determines the growth length of the long bone as well as the growth direction of the long bone. The epiphyseal plate is composed of orderly stacking layers of chondrocytes with different maturity. The chondrocytes on the side near the diaphysis continue to mature, and the mature chondrocytes are transformed into osteoblasts. With the calcification of the surrounding matrix, the formed cancellous bone is added to the both ends of the long bone, thus increasing the length of the long bone. Under normal cases, the growth of the epiphyseal plate is balanced.

However, in the case of trauma or osteopathy, the growth of the epiphyseal plate is prone to imbalance, resulting in asymmetric growth of skeletons, that is, the growth direction and the growth speed of the long bone change. The disproportionate growth of the medial and lateral epiphysis of the distal tibia leads to the varus deformity and the valgus deformity of the ankle joint. In clinical medical treatment, the technique of guided growth is usually used to correct the varus deformity and the valgus deformity of the ankle joint.

Conventional 8-shaped steel plate epiphyseal plate arrest technique refers to that the 8-shaped steel plate is attached to the metaphysis and the epiphysis which are at one side of the epiphyseal plate, and is fixed by two screws parallel to the epiphyseal plate, thus limiting the growth speed of the one side of the epiphyseal plate, which is often used to correct the angulation deformity of ankle valgus and ankle varus. When the patient suffers from ankle valgus, the medial malleolus prominence is remarkable. When the 8-shaped steel plate is placed after incision of the skin, as the 8-shaped steel plate is straight and has a certain width and thickness, after the steel plate is placed, the tension of the skin incision at the medial malleolus is too high, and the skin suture is difficult. After barely suturing, the tension of the skin is high, which leads to the difficulty of skin healing after operation, and even the incision dehiscence and the exposure of the steel plate, resulting in serious complications. In addition, the arrest means of penetrating the epiphyseal plate by one screw is adopted, which has the risk of premature closure of the epiphyseal plate, and is not suitable for the medial epiphyseal plate arrest of the distal tibia in young children with ankle valgus.

SUMMARY

The technical problem to be solved by the present disclosure is to overcome the shortcomings in the prior art, a distal medial tibial hemi-epiphysiodesis blocking staple and supporting tools are provided. The design feature is suitable for anatomical structures of the medial metaphysis and the epiphysis of the distal tibia, the installation is convenient and firm, and the medial hemi-epiphysiodesis blocking staple clings to the skeleton, is small in volume after being installed, and thus there are no problems such as difficult suturing of incision and exposure of internal fixation caused by skin dehiscence.

To achieve the objective above, the present disclosure employs the following technical solution.

A distal medial tibial hemi-epiphysiodesis blocking staple includes a tibial arm for being implanted into medial metaphysis of distal tibia, an epiphyseal arm for being implanted into epiphysis, and a connecting section for being externally placed outside the distal tibia and the epiphyseal and straddling an epiphyseal plate. Both ends of the connecting section are connected with the tibial arm and the epiphyseal arm respectively to form a generally U-shape. The tibial arm and the epiphyseal arm are arranged in parallel and in arc transition with the connecting section to limit a spacing between the distal tibia and the epiphysis, and inverted tooth portions for preventing the hemi-epiphysiodesis blocking staple from withdrawing are uniformly distributed on the tibial arm and the epiphyseal arm.

As a further improvement of the technical solution above.

A tip portion connected with a corresponding one of the inverted tooth portions is provided at a tail end of each of the tibial arm and the epiphyseal arm.

The inverted tooth portions include multiple tooth tips, the multiple tooth tips are uniformly arranged in an implantation direction, and each of the multiple tooth tips has an inverted tooth shape in a direction opposite to the implantation direction.

Each of the multiple tooth tips is formed by connecting a first inclined plane and a second inclined plane, the first inclined plane is adjacent to the tip portion, and the second inclined plane is far away from the tip portion.

A width of the first inclined plane in the implantation direction is greater than a width of the second inclined plane in the implantation direction.

The inverted tooth portions are located on a side, that faces the epiphyseal arm, of the tibial arm and a side, that faces the tibial arm, of the epiphyseal arm.

The tibial arm and the epiphyseal arm are implanted into the distal tibia and the epiphysis in a horizontal direction, respectively, and the connecting section is generally attached to an outer surface of the distal tibia and an outer surface of the epiphysis.

A cross section of each of the tibial arm and the epiphyseal arm in an implantation direction is obliquely quadrilateral and is in fillet transition with the connecting section; and a length of the tibial arm is smaller than a length of the epiphyseal arm.

A supporting tool of a distal medial tibial hemi-epiphysiodesis blocking staple includes a drill sleeve. The drill sleeve includes drill base provided with a handle, the drill base is provided with a positioning chisel bit for positioning implantation points on the distal tibia and the epiphysis, and at least one guide hole penetrating to the positioning chisel bit. A guide pin is configured to be freely inserted into the guide hole for punching a hole at a corresponding one of the implantation points.

A supporting tool of a distal medial tibial hemi-epiphysiodesis blocking staple includes a driver. The driver includes a socket provided with a handle portion. An end, far away from the handle portion, of the socket is provided with a notch for accommodating the connecting section, and the notch is enabled to push the connecting section by operating the handle portion to implant the tibial arm into the distal tibia and implant the epiphyseal arm into the epiphysis.

Compared with the prior art, the embodiments have beneficial effects as follows.

Through the tibia arm and the epiphyseal arm, the hemi-epiphysiodesis blocking staple can be conveniently implanted from implantation holes pre-drilled in the metaphyseal tibia and the epiphysis, making the installation convenient. The inverted tooth portions on the tibia arm and the epiphyseal arm can prevent the inserted hemi-epiphysiodesis blocking staple from displacing even withdrawing. An angle between the tibial arm and the connecting section and an angle between the epiphyseal arm and the connecting section are designed according to an angle between a distal medial tibial cortex and an epiphyseal plate plane of a child in clinic, such that the implanted hemi-epiphysiodesis blocking staple can be in fit with the skeletal morphology of the distal medial tibia to the greatest extent, and the occurrence of complications, such as difficult suturing of incision after operation and wound dehiscence caused by excessive incision tension, is reduced. The arrest effect is good, and the patient can quickly return to normal daily life.

LIST OF THE REFERENCE CHARACTERS

100 distal tibia; 200 epiphysis; 201 epiphyseal plate; 1 tibial arm; 2 epiphyseal arm; 3 connecting section; 4 inverted tooth portion; 41 tooth tip; 42 first inclined plane; 43 second inclined plane; 5 tip portion; 6 drill sleeve; 61 handle; 62 drill base; 621 positioning chisel bit; 622 guide hole; 7 driver; 71 handle portion; 72 socket; 73 notch; 74 tangent plane.

DETAILED DESCRIPTION OF THE EMBODIMENTS

The present disclosure is further described below with reference to accompanying drawings and specific embodiments.

Figure 1:
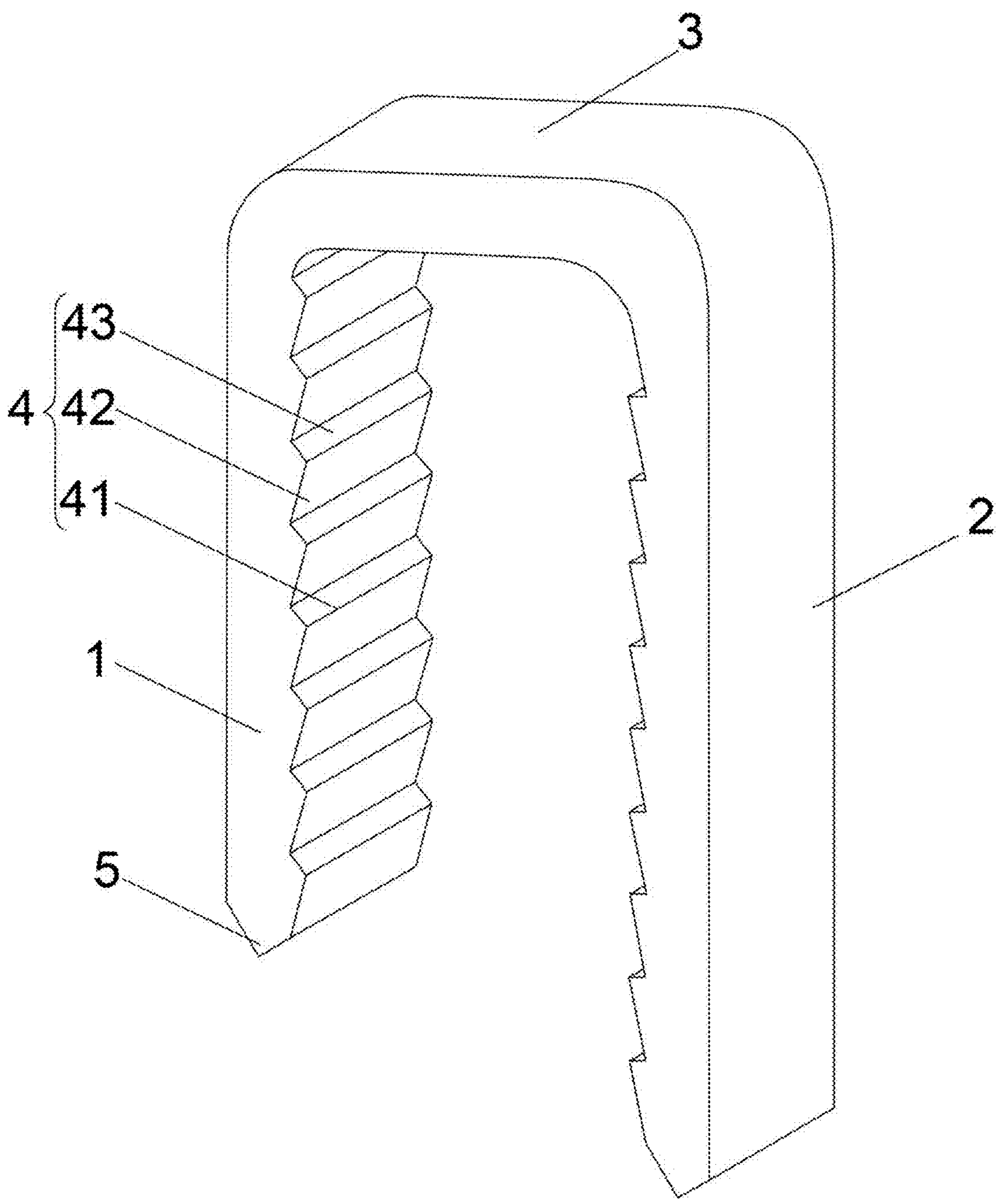
FIG. 1 is a structural diagram of a distal medial tibial hemi-epiphysiodesis blocking staple.
Figure 2:
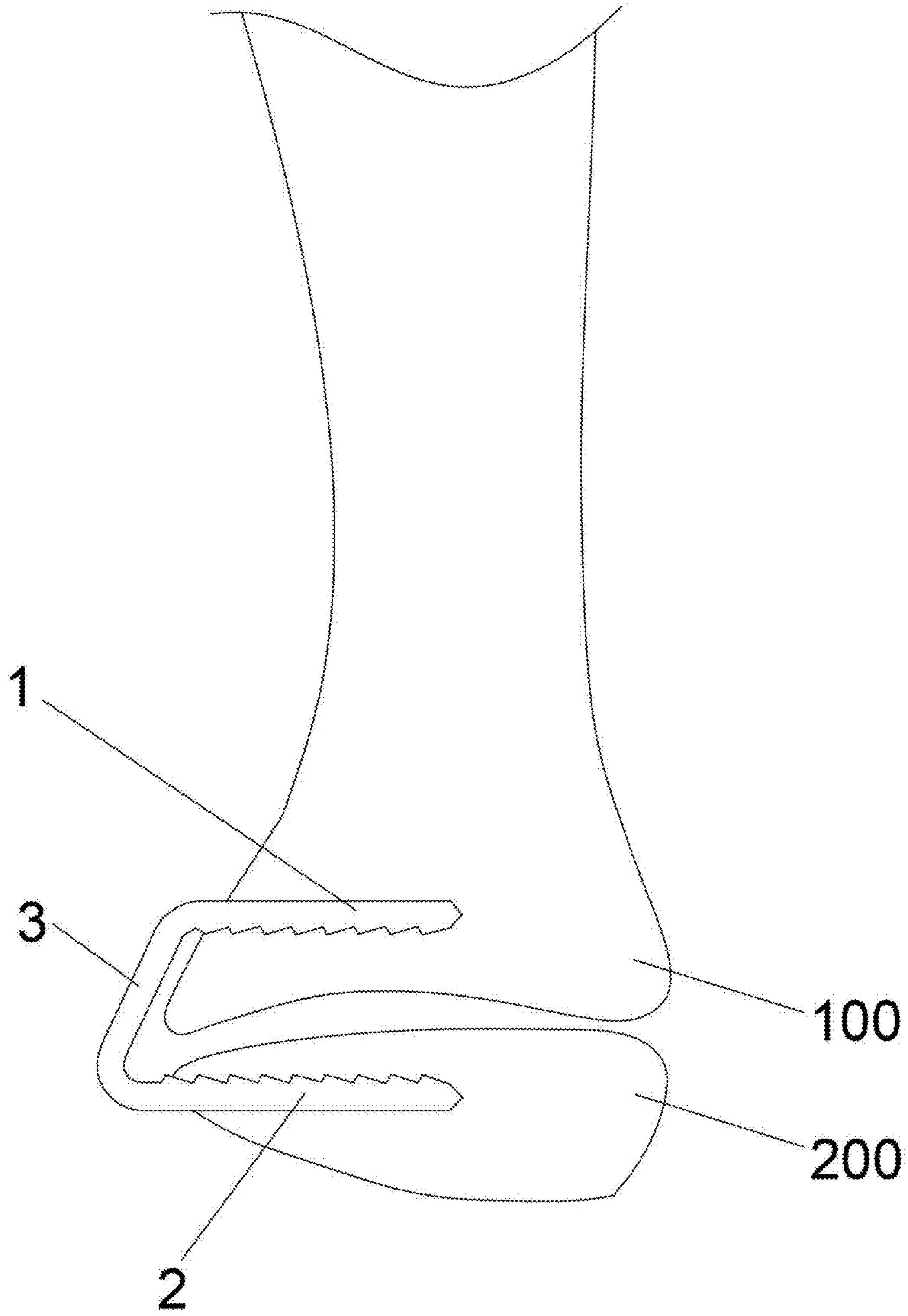
FIG. 2 is a structural diagram of an installation of the distal medial tibial hemi-epiphysiodesis blocking staple.

As shown in FIG. 1 and FIG. 2, a distal medial tibial hemi-epiphysiodesis blocking staple includes a tibial arm 1 for being implanted into medial metaphysis of distal tibia 100, an epiphyseal arm 2 for being implanted into epiphysis 200, and a connecting section 3 for being externally placed outside the distal tibia 100 and the epiphyseal 200 and straddling an epiphyseal plate 201. Both ends of the connecting section 3 are connected with the tibial arm 1 and the epiphyseal arm 2 respectively to form a generally U-shape. The tibial arm 1 and the epiphyseal arm 2 are arranged in parallel and in arc transition with the connecting section 3 to limit a spacing between the distal tibia 100 and the epiphysis 200. Inverted tooth portions 4 for preventing the hemi-epiphysiodesis blocking staple from withdrawing are uniformly distributed on the tibial arm 1 and the epiphyseal arm 2. Through the tibia arm and the epiphyseal arm, the hemi-epiphysiodesis blocking staple can be conveniently implanted from implantation holes pre-drilled in metaphyseal tibia and epiphysis, making the installation convenient. The inverted tooth portions can prevent the implanted hemi-epiphysiodesis blocking staple from displacing even withdrawing, and the firm connection is achieved by the connecting section. The overall volume of the hemi-epiphysiodesis blocking staple after installing is small, without affecting the suture and healing of the incision. An angle between the tibial arm 1 and the connecting section 3 and an angle between the epiphyseal arm 2 and the connecting section 3 are designed according to an angle between a distal medial tibial cortex and an epiphyseal plate plane of a child in clinic, such that the implanted hemi-epiphysiodesis blocking staple can be in fit with the skeletal morphology of the distal medial tibia to the greatest extent, and the occurrence of complications, such as difficult suturing of incision after operation and wound dehiscence caused by excessive incision tension, is reduced. The arrest effect is good, and the patient can quickly return to normal daily life.

In this embodiment, a tip portion 5 connected with the inverted tooth portion 4 is provided at a tail end of each of the tibial arm 1 and the epiphyseal arm 2. Through the tip portion 5, the hemi-epiphysiodesis blocking staple can be conveniently inserted into the implantation holes pre-drilled in the tibial arm 1 and the epiphyseal arm 2, thus further improving the convenience of installation.

In this embodiment, the inverted tooth portion 4 includes multiple tooth tips 41, the multiple tooth tips 41 are uniformly arranged in an implantation direction, and each tooth tip 41 has an inverted tooth shape in a direction opposite to the implantation direction. Through the multiple tooth tips 41 forming inverted tooth shapes, the installation firmness of the distal medial tibial hemi-epiphysiodesis blocking staple and a supporting tool thereof can be further improved.

In this embodiment, each tooth tip 41 is formed by connecting a first inclined plane 42 and a second inclined plane 43, and the first inclined plane 42 is adjacent to the tip portion 5, and the second inclined plane 43 is far away from the tip portion 5. The providing of the first inclined plane 42 and the second inclined plane 43 facilitates the processing and manufacturing, and reduces the manufacturing cost.

In this embodiment, a width of the first inclined plane 42 in the implantation direction is greater than a width of the second inclined plane 43 in the implantation direction. The wider first inclined plane 42 is beneficial for the hemi-epiphysiodesis blocking staple to quickly deep into the implantation hole, and the narrower second inclined plane 43 can prevent the hemi-epiphysiodesis blocking staple from slightly displacing.

In this embodiment, the inverted tooth portions 4 are located on a side, that faces the epiphyseal arm 2, of the tibial arm 1 and a side, that faces the tibial arm 1, of the epiphyseal arm 2. The inverted tooth portions 4 are arranged in opposite, which makes the force for preventing the tibial arm 1 and the epiphyseal arm 2 from withdrawing from the bone more concentrated and effective.

In this embodiment, the tibial arm 1 and the epiphyseal arm 2 are implanted into the distal tibia 100 and the epiphysis 200 in a horizontal direction, respectively, and the connecting section 3 is generally attached to an outer surface of the distal tibia 100 and an outer surface of the epiphysis 200. The tibial arm 1 and the epiphyseal arm 2 arranged horizontally are facilitated to deep into the bone along the implantation holes, and the connecting section 3 is attached to the outer surface of the bone, which can further reduce the volume and contribute to the suture of the incision.

In this embodiment, the cross section of each of the tibial arm 1 and the epiphyseal arm 2 in the implantation direction is quadrilateral, and is in fillet transition with the connecting section 3, and a length of the tibial arm 1 is smaller than a length of the epiphyseal arm 2. The quadrilateral section is generally quadrangular, and a structure thereof is more stable, thus avoiding deformation or unstable installation. A difference in length between the tibial arm 1 and the epiphyseal arm 2 is set according to a difference between the distal tibia 100 and the epiphysis 200.

Figure 3:
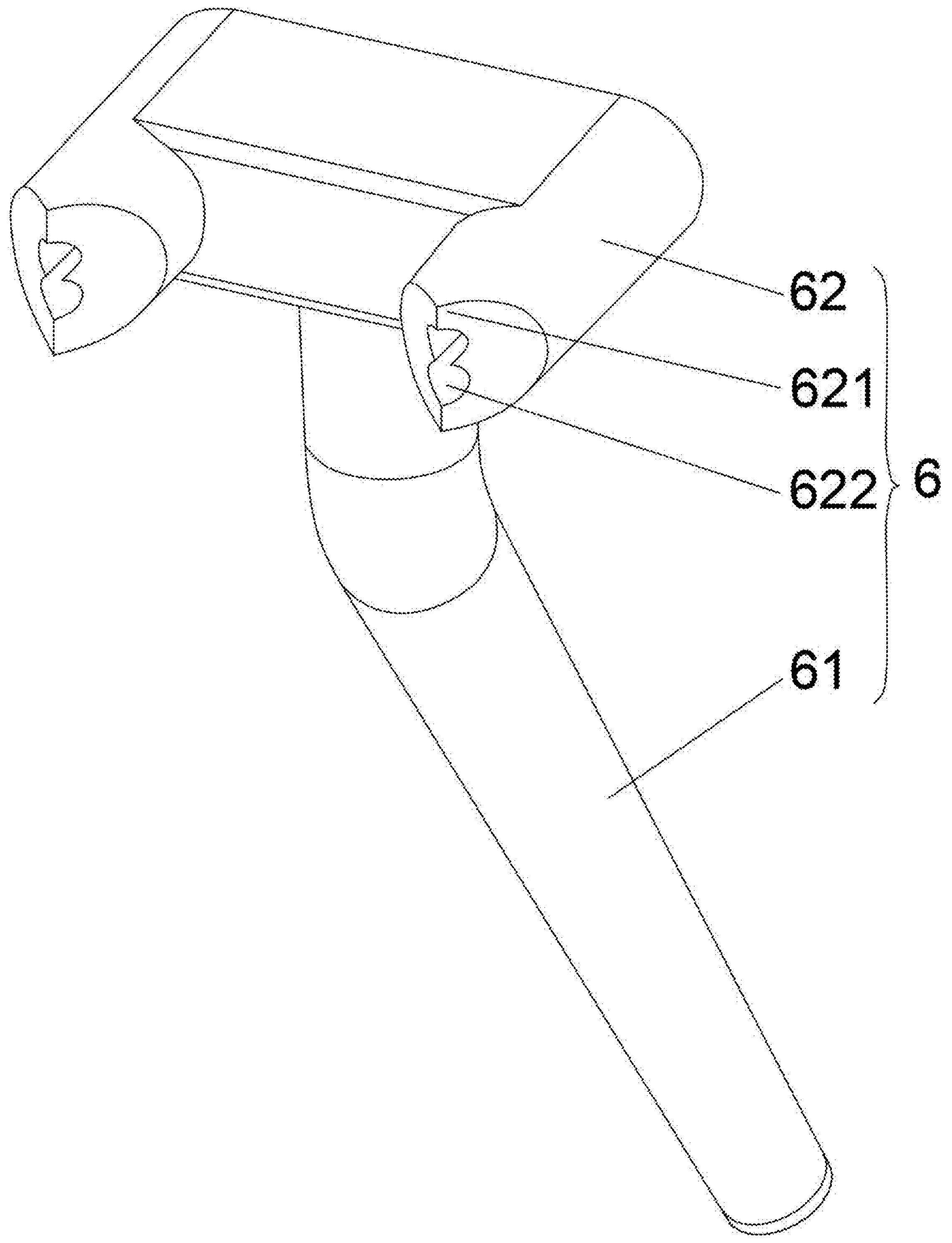
FIG. 3 is a structural diagram of a drill sleeve.

As shown in FIG. 3, a supporting tool of a distal medial tibial hemi-epiphysiodesis blocking staple in this embodiment includes a drill sleeve 6. The drill sleeve 6 includes a drill base 62 provided with a handle 61. The drill base 62 is provided with a positioning chisel bit 621 for positioning implantation points on the distal tibia 100 and the epiphysis 200, and at least one guide hole 622 penetrating to the positioning chisel bit 621. The guide pin 622 is configured to be freely inserted into the guide hole 622 for punching a hole at the implantation point. A U-shaped staple has a width of 3 mm and a thickness of 1.5 mm, and a spacing between the tibial arm 1 and the epiphyseal arm 2 is 10 mm. There are two guide holes 622, which are in a shape of "8" as a whole, and thus the guide pins with a diameter of 1.5 mm can be freely inserted. During operation, two positioning chisel bits 621 on the drill sleeve 6 are aligned with the selected two implantation points on the distal tibia 100 and the epiphysis 200 up and down, respectively, and the guide pins can be inserted into the guide holes 622 to an appropriate depth of the implantation points, and then pulled out.

Figure 4:
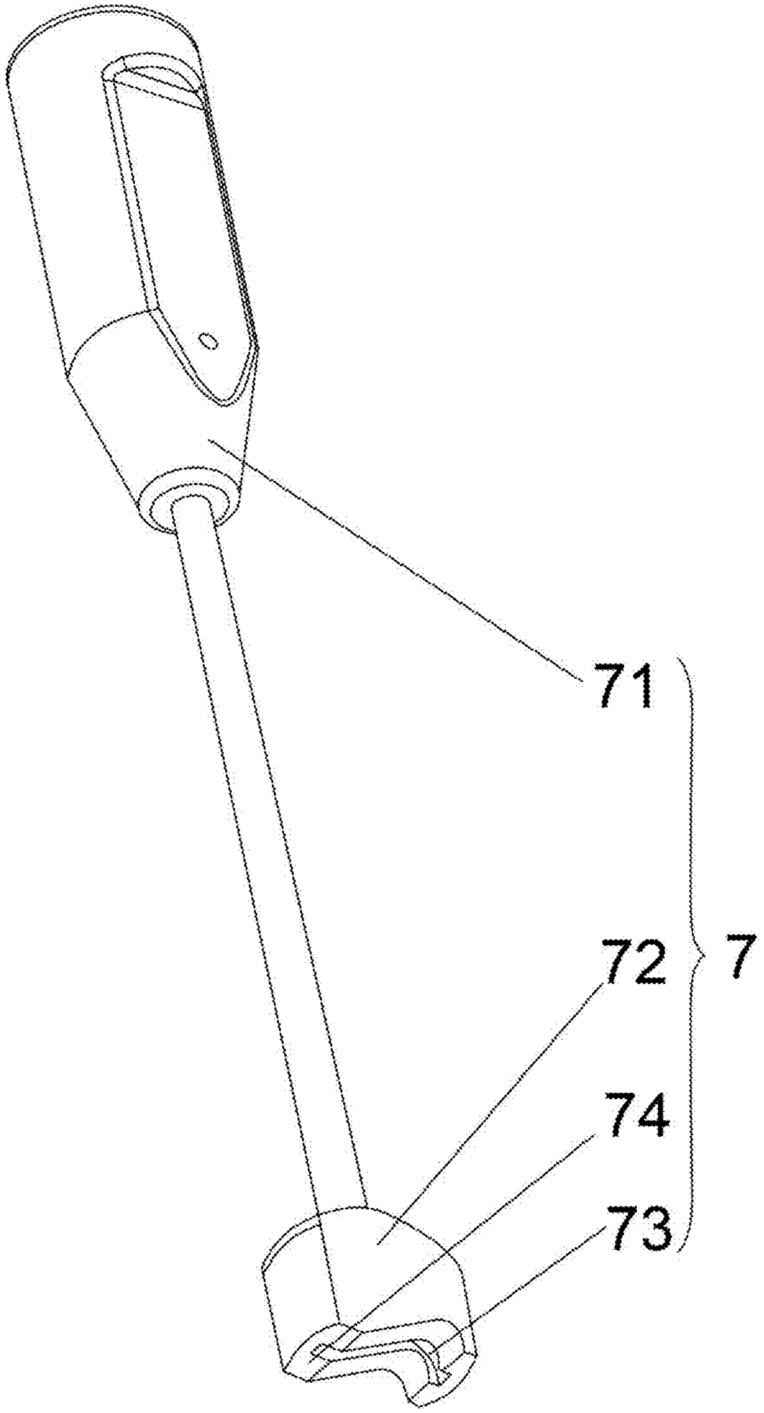
FIG. 4 is a structural diagram of a driver.

As shown in FIG. 4, a supporting tool of a distal medial tibial hemi-epiphysiodesis blocking staple includes a driver 7. The driver 7 includes a socket 72 provided with a handle portion 71. An end, far away from the handle portion 71, of the socket 72 is provided with a notch 73 for accommodating the connecting section 3, and the notch 73 is enabled to push the connecting section 3 by operating the handle portion 71 to implant the tibial arm 1 into the distal tibia 100 and implanting the epiphyseal arm 2 into the epiphysis 200. After punching holes in the upper implantation point and the lower implantation point, the tip portions 5 of the U-shaped staple are inserted into the corresponding implantation points, during insertion, the driver 7 is applied, and corners for connecting the connecting section 3 to the tibial arm 1 and the epiphyseal arm 2 are covered by the notch 73, and the handle portion 71 is tapped to insert the tibial arm 1 and the epiphyseal arm 2 to a proper depth. The socket 73 is in a shape of "7" and corresponds to the corners for connecting the connecting section 3 to the tibial arm 1 and the epiphyseal arm 2, and one side, adjacent to the connecting section 3, of the notch 73 is provided with a tangent plane 74, and the connecting section 3 can be conveniently clamped with and separated from the connecting section 3 through the tangent plane 74.

The above is only the preferred embodiment of the present disclosure, and the scope of protection of the present disclosure is not limited to the above embodiments. For those of ordinary skill in the art, various improvements and changes made without departing from the technical concept of the present disclosure shall be regarded as the scope of protection of the present disclosure.

What is claimed is:

1. A distal medial tibial hemi-epiphysiodesis blocking staple, comprising a tibial arm (1) for being implanted into medial metaphysis of distal tibia (100), an epiphyseal arm (2) for being implanted into epiphysis (200), and a connecting section (3) for being externally placed outside the distal tibia (100) and the epiphyseal (200) and straddling an epiphyseal plate (201), wherein both ends of the connecting section (3) are connected with the tibial arm (1) and the epiphyseal arm (2) respectively to form a generally U-shape; the tibial arm (1) and the epiphyseal arm (2) are arranged in parallel and in arc transition with the connecting section (3) to limit a spacing between the distal tibia (100) and the epiphysis (200), and inverted tooth portions (4) for preventing the hemi-epiphysiodesis blocking staple from withdrawing are uniformly distributed on the tibial arm (1) and the epiphyseal arm (2); an angle between the tibial arm and the connecting section and an angle between the epiphyseal arm and the connecting section are configured to be designed according to an angle between a distal medial tibial cortex and an epiphyseal plate plane of a child in clinic, such that a implanted hemi-epiphysiodesis blocking staple is able to be in fit with a skeletal morphology of a distal medial tibia.

2. The distal medial tibial hemi-epiphysiodesis blocking staple according to claim 1, wherein a tip portion (5) connected with a corresponding one of the inverted tooth portions (4) is provided at a tail end of each of the tibial arm (1) and the epiphyseal arm (2).

3. The distal medial tibial hemi-epiphysiodesis blocking staple according to claim 2, wherein the inverted tooth portions (4) comprise a plurality of tooth tips (41), the plurality of tooth tips (41) are uniformly arranged in an implantation direction, and each of the plurality of tooth tips (41) has an inverted tooth shape in a direction opposite to the implantation direction.

4. The distal medial tibial hemi-epiphysiodesis blocking staple according to claim 3, wherein each of the plurality of tooth tips (41) is formed by connecting a first inclined plane (42) and a second inclined plane (43), the first inclined plane (42) is adjacent to the tip portion (5), and the second inclined plane (43) is far away from the tip portion (5).

5. The distal medial tibial hemi-epiphysiodesis blocking staple according to claim 4, wherein a width of the first inclined plane (42) in the implantation direction is greater than a width of the second inclined plane (43) in the implantation direction.

6. The distal medial tibial hemi-epiphysiodesis blocking staple according to claim 2, wherein the inverted tooth portions (4) are located on a side, that faces the epiphyseal arm (2), of the tibial arm (1) and a side, that faces the tibial arm (1), of the epiphyseal arm (2).

7. The distal medial tibial hemi-epiphysiodesis blocking staple according to claim 1, wherein the tibial arm (1) and the epiphyseal arm (2) are implanted into the distal tibia (100) and the epiphysis (200) in a horizontal direction, respectively, and the connecting section (3) is generally attached to an outer surface of the distal tibia (100) and an outer surface of the epiphysis (200).

8. The distal medial tibial hemi-epiphysiodesis blocking staple according to claim 1, wherein a cross section of each of the tibial arm (1) and the epiphyseal arm (2) in an implantation direction is obliquely quadrilateral and is in fillet transition with the connecting section (3); and a length of the tibial arm (1) is smaller than a length of the epiphyseal arm (2).

9. A supporting tool of a distal medial tibial hemi-epiphysiodesis blocking staple according to claim 1, comprising a drill sleeve (6), wherein the drill sleeve (6) comprises a drill base (62) provided with a handle (61), the drill base (62) is provided with a positioning chisel bit (621) for positioning implantation points on the distal tibia (100) and the epiphysis (200), and at least one guide hole (622) penetrating to the positioning chisel bit (621); and a guide pin is configured to be freely inserted into the guide hole (622) for punching a hole at a corresponding one of the implantation points.

10. The supporting tool of a distal medial tibial hemi-epiphysiodesis blocking staple according to claim 9, wherein a tip portion (5) connected with a corresponding one of the inverted tooth portions (4) is provided at a tail end of each of the tibial arm (1) and the epiphyseal arm (2).

11. The supporting tool of a distal medial tibial hemi-epiphysiodesis blocking staple according to claim 10, wherein the inverted tooth portions (4) comprise a plurality of tooth tips (41), the plurality of tooth tips (41) are uniformly arranged in an implantation direction, and each of the plurality of tooth tips (41) has an inverted tooth shape in a direction opposite to the implantation direction.

12. The supporting tool of a distal medial tibial hemi-epiphysiodesis blocking staple according to claim 11, wherein each of the plurality of tooth tips (41) is formed by connecting a first inclined plane (42) and a second inclined plane (43), the first inclined plane (42) is adjacent to the tip portion (5), and the second inclined plane (43) is far away from the tip portion (5).

13. The supporting tool of a distal medial tibial hemi-epiphysiodesis blocking staple according to claim 12, wherein a width of the first inclined plane (42) in the implantation direction is greater than a width of the second inclined plane (43) in the implantation direction.

14. The supporting tool of a distal medial tibial hemi-epiphysiodesis blocking staple according to claim 10, wherein the inverted tooth portions (4) are located on a side, that faces the epiphyseal arm (2), of the tibial arm (1) and a side, that faces the tibial arm (1), of the epiphyseal arm (2).

15. The supporting tool of a distal medial tibial hemi-epiphysiodesis blocking staple according to claim 9, wherein the tibial arm (1) and the epiphyseal arm (2) are implanted into the distal tibia (100) and the epiphysis (200) in a horizontal direction, respectively, and the connecting section (3) is generally attached to an outer surface of the distal tibia (100) and an outer surface of the epiphysis (200).

16. The supporting tool of a distal medial tibial hemi-epiphysiodesis blocking staple according to claim 9, wherein a cross section of each of the tibial arm (1) and the epiphyseal arm (2) in an implantation direction is obliquely quadrilateral and is in fillet transition with the connecting section (3); and a length of the tibial arm (1) is smaller than a length of the epiphyseal arm (2).

17. A supporting tool of a distal medial tibial hemi-epiphysiodesis blocking staple according to claim 1, comprising a driver (7), wherein the driver (7) comprises a socket (72) provided with a handle portion (71); an end, far away from the handle portion (71), of the socket (72) is provided with a notch (73) for accommodating the connecting section (3), and the notch (73) is enabled to push the connecting section (3) by operating the handle portion (71) to implant the tibial arm (1) into the distal tibia (100) and implant the epiphyseal arm (2) into the epiphysis (200).

18. The supporting tool of a distal medial tibial hemi-epiphysiodesis blocking staple according to claim 17, wherein a tip portion (5) connected with a corresponding one of the inverted tooth portions (4) is provided at a tail end of each of the tibial arm (1) and the epiphyseal arm (2).

19. The supporting tool of a distal medial tibial hemi-epiphysiodesis blocking staple according to claim 18, wherein the inverted tooth portions (4) comprise a plurality of tooth tips (41), the plurality of tooth tips (41) are uniformly arranged in an implantation direction, and each of the plurality of tooth tips (41) has an inverted tooth shape in a direction opposite to the implantation direction.

20. The supporting tool of a distal medial tibial hemi-epiphysiodesis blocking staple according to claim 19, wherein each of the plurality of tooth tips (41) is formed by connecting a first inclined plane (42) and a second inclined plane (43), the first inclined plane (42) is adjacent to the tip portion (5), and the second inclined plane (43) is far away from the tip portion (5).

* * * * *